(12) United States Patent
Saruwatari

(10) Patent No.: US 6,414,199 B1
(45) Date of Patent: Jul. 2, 2002

(54) METHOD OF PRODUCING BISPHENOL A

(75) Inventor: Tetsuya Saruwatari, Tokuyama (JP)

(73) Assignee: Idemitsu Petrochemical Co., Ltd., Tokyo (JP)

( * ) Notice: Subject to any disclaimer, the term of this patent is extended or adjusted under 35 U.S.C. 154(b) by 0 days.

(21) Appl. No.: 09/719,169

(22) PCT Filed: Apr. 12, 2000

(86) PCT No.: PCT/JP00/02375

§ 371 (c)(1),
(2), (4) Date: Dec. 13, 2000

(87) PCT Pub. No.: WO00/61532

PCT Pub. Date: Oct. 19, 2000

(30) Foreign Application Priority Data

Apr. 13, 1999 (JP) .......................................... 11-105472

(51) Int. Cl.$^7$ .............................................. C07C 37/20
(52) U.S. Cl. ..................................................... 568/728
(58) Field of Search ......................................... 568/728

(56) References Cited

U.S. PATENT DOCUMENTS 2,775,620 A * 12/1956 Williamson ................. 568/728
4,308,405 A    12/1981 Kwantes
4,859,803 A *  8/1989 Shaw .......................... 568/728
6,211,417 B1 *  4/2001 Fengler ....................... 568/728

FOREIGN PATENT DOCUMENTS

| EP | 0 754 666 A2 |   | 7/1996 |
| EP | 754666 A | * | 1/1997 |
| GB | 1185102 A | * | 3/1970 |
| JP | 6-92889 A |   | 4/1994 |
| JP | 9-31002 A |   | 2/1997 |

* cited by examiner

Primary Examiner—Michael L. Shippen
(74) Attorney, Agent, or Firm—Oblon, Spivak, McClelland, Maier & Neustadt, P.C.

(57) ABSTRACT

Provided is a method of producing bisphenol A in which the life of the acid-type ion-exchange resin used as a catalyst can be prolonged. The method comprises reacting phenol and acetone in the presence of an acid-type ion-exchange resin serving as a catalyst and an alkylmercaptan serving as a promoter to give bisphenol A, in which three or more reactors connected in series are used and all of phenol, all of an alkylmercaptan and a part of acetone are fed into the first reactor while the remaining acetone, divided into plural portions, is into all the second to the last reactors.

16 Claims, 1 Drawing Sheet

METHOD OF PRODUCING BISPHENOL A

TECHNICAL FIELD

The present invention relates to a process for producing bisphenol A in which the life of the acid-type ion-exchange resin used as a catalyst can be prolonged.

BACKGROUND ART

Bisphenol A [that is, 2,2-bis (4-hydroxyphenyl)propane] is an important starting compound for engineering plastics such as polycarbonate resins, polyarylate resins and others and for epoxy resins, etc. There is increasing the demand for bisphenol A with the increase in the production of such resins.

It is known that bisphenol A is produced by reacting acetone with excess of phenol in the presence of an acid-type ion-exchange resin catalyst and a sulfur compound promoter such as alkylmercaptans, etc. In this reaction, the acid-type ion-exchange resin catalyst used degrades time-dependently. The primary reason for it will be heavy substances derived from acetone. The degradation of the catalyst starts around the inlet of the reactor. Since the degradation speed is high, excess of the catalyst shall be filled into the reactor to ensure long-run continuous operation. In order to keep the intended output of bisphenol A being produced (that is, in order to keep the conversion of phenol being reacted) even after the catalyst used has degraded, acetone to be fed into the reactor must be increased time-dependently. Since the non-reacted acetone must be recovered from the reaction mixture through distillation, the amount of acetone to be increased shall be limited depending on the capability of the distillation unit used. In other words, the catalyst must be exchanged for a fresh one when the capability of the distillation unit has reached its limit. Accordingly, properly controlling the reaction condition so as to prolong as much as possible the life of the catalyst being used could reduce the frequency of catalyst exchange, thereby reducing the production costs. In this connection, methods of using a plurality of reactors to control the reaction condition are proposed in Japanese Patent Laid-Open Nos. 19952/1979 and 17144/1990.

In the method proposed in Japanese Patent Laid-Open No. 19952/1979, two or more reactors are disposed in series, and a carbonyl compound, divided into plural portions, is added to each reactor whereby the concentration of the bisphenol product in the fluid from the latter reaction zone is substantially increased with no negative influences on the properties of the ion-exchange resin catalyst used and the properties of the phenol recovered. However, in the method concretely illustrated therein, a single reactor is used, and nothing is disclosed therein that relates to the high-level phenol conversion attained by the present invention.

The method proposed in Japanese Patent Laid-Open No. 17144/1990 comprises adding an alkylmercaptan, divided in plural portions, to a series of reactors to thereby inhibit the formation of cyclic diner by-products. In the method disclosed therein, used is two reactors for producing bisphenol A. However, in the method disclosed, used is a large amount of methylmercaptan that reaches 50% by weight of the reaction product. In this, therefore, there is little possibility of increased phenol conversion, and the life of the catalyst used could not be prolonged so much.

In the situation as above, the present invention is to provide a method of producing bisphenol A in which the life of the acid-type ion-exchange catalyst used can be prolonged.

DISCLOSURE OF THE INVENTION

We, the present inventor have assiduously studied the outstanding problems in the art, and have found that, when three or more reactors connected in series are used in such a manner that all of phenol, all of an alkylmercaptan and a part of acetone are fed into the first reactor while the remaining acetone, divided into plural portions, is into all the second to the last reactors, then an increased phenol conversion can be ensured. On the basis of this finding, we have completed the present invention.

Specifically, the invention is to provide a method of producing bisphenol A by reacting phenol and acetone in the presence of an acid-type ion-exchange resin serving as a catalyst and an alkylmercaptan serving as a promoter, in which three or more reactors connected in series are used and all of phenol, all of an alkylmercaptan and a part of acetone are fed into the first reactor while the remaining acetone, divided into plural portions, is into all the second to the last reactors to produce bisphenol A.

BEST MODES OF CARRYING OUT THE INVENTION

Figure 1:
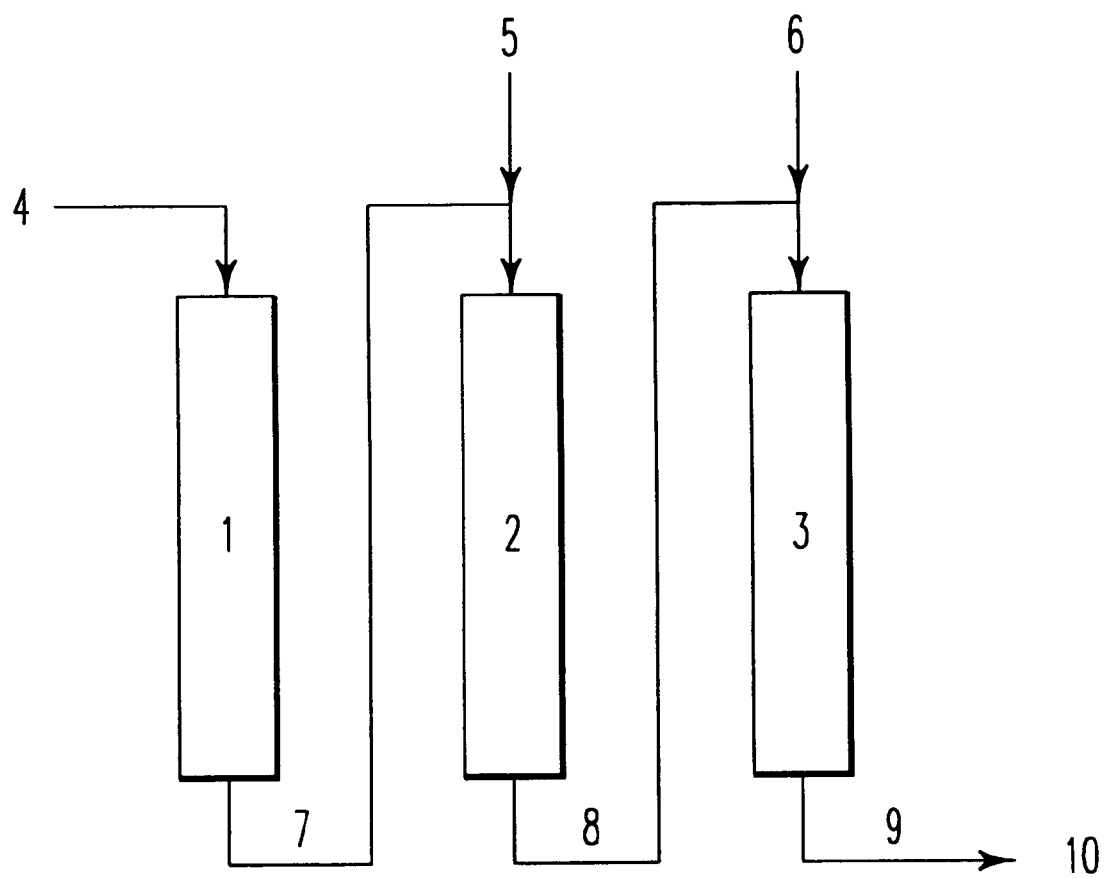
FIG. 1 is one example of the reaction flowchart of the method of the invention.

The invention is described in detail hereinunder.

In the invention, bisphenol A is produced by reacting acetone with excess of phenol in the presence of an acid-type ion-exchange resin serving as a catalyst and an alkylmercaptan serving as a promoter.

The acid-type ion-exchange resin to be used as the catalyst is preferably a sulfonic acid-type cation-exchange catalyst. Concretely, it includes, for example, sulfonated styrene-divinylbenzene copolymers, sulfonated crosslinked styrene polymers, phenol-formaldehyde-sulfonic acid resins, benzene-formaldehyde-sulfonic acid resins, etc. These may be used either singly or as combined.

The alkylmercaptan to be used as the promoter is preferably a mercaptan having a C1–10 alkyl group. Concretely, it includes, for example, methylmercaptan, ethylmercaptan, propylmercaptan, octylmercaptan, cyclohexylmercaptan, etc. Of these, especially preferred is ethylmercaptan. These alkylmercaptans may be used either singly or as combined.

In the invention, used are three or more reactors connected in series in the step of reacting phenol with acetone. In this, all of phenol, all of an alkylmercaptan and a part of acetone are fed into the first reactor while the remaining acetone, divided into plural portions, is into all the second to last reactors. In other words, acetone is divided into plural portions and the necessary amount thereof is fed into each reactor. Not interfering with the object of the invention, part of phenol and an alkylmercaptan, both divided into plural portions, could be fed into any of the second to last reactors.

Advantageously, the specific feeding mode prevents the catalyst used from being degraded probably by acetone-derived heavy substances. The effect is remarkable when at least three reactors are used in the method of the invention.

The reactors for use here in are not specifically defined, but preferred are fixed-bed reactors for preventing the catalyst used from powdering.

Preferably, the reaction temperature falls between 60 and 100° C., more preferably between 65 and 95° C. If the reaction temperature is too low, it is unfavorable since the phenol phase will solidify; but if too high, it is also unfavorable since the ion-exchange resin used will much degrade.

Preferably, the molar ratio of all acetone/mercaptan falls between 10 and 25. If the ratio is smaller than 10, it is unfavorable since the color hue of the product, bisphenol A will be unstable; but if larger than 25, it is also unfavorable since the reaction is retarded and the reaction selectively will be low. Especially preferably, the ratio falls between 15 and 20. All acetone referred to herein is the total amount of acetone portions to be fed into the individual reactors.

Preferably, the molar ratio of phenol/all acetone falls between 6 and 13. If the ratio is smaller than 6, it is unfavorable since the color hue of the product, bisphenol A will be unstable; but if larger than 13, it is also unfavorable since the reaction is retarded and the amount of phenol to be recovered will increase. Especially preferably, the ratio falls between 8 and 12.

The amount of acetone to be fed into each reactor is not specifically defined. For example, from 30 to 50% of all acetone will be fed into the first reactor, and the remaining amount thereof, equally divided into plural portions, will be fed into the second to last reactors. FIG. 1 shows one example of the reaction flowchart of the method of the invention, in which are used three reactors.

Preferably, the liquid hourly space velocity (LHSV) in each reactor falls between 0.2 and 30 $hr^{-1}$, more preferably between 0.5 and 6 $hr^{-1}$.

With reference to FIG. 1, one embodiment of the method of producing bisphenol A of the invention is described. The first reactor 1, the second reactor 2 and the third reactor 3 are all fixed-bed reactors, each of which is filled with an acid-type ion-exchange resin. A starting material mixture 4 as prepared by mixing a promoter, alkylmercaptan and starting compounds, phenol and acetone is fed into the first reactor 1.

The flow 7 from the first reactor 1 is, after mixed with acetone 5, introduced into the second reactor 2. Similarly, the flow 8 from the second reactor 2 is, after mixed with acetone 6, introduced into the third reactor 3. The flow 9 from the third reactor 3 is transferred into the next step 10.

The reaction mixture from phenol and acetone contains not only the product, bisphenol A but also the non-reacted phenol, the non-reacted acetone, the alkylmercaptan used in the system, and by-products such as water, organic sulfur compounds except the alkylmercaptan, coloring substances, etc. Therefore, the substances except bisphenol A must be removed from the reaction mixture.

From the reaction mixture, the non-reacted acetone, the by-product water, the alkylmercaptan and others are removed through distillation under reduced pressure. For this, a distillation tower may be used, and the non-reacted acetone, the by-product water, the alkylmercaptan and others are evaporated away through its top while a liquid mixture containing bisphenol A, phenol and others is taken out through its bottom. The reduced pressure for distillation may fall between 50 and 600 Torr, and the temperature may fall between 70 and 180° C. When the non-reacted acetone, the by-product water and the alkylmercaptan are removed by the use of such a distillation tower under the condition as above, the non-reacted phenol will form an azeotropic mixture with the vaporizing components and will be partly removed out of the system through the top of the tower.

From the reaction mixture, removed are the vaporizing components as above, and phenol is then removed from the remaining liquid mixture through distillation under reduced pressure whereby bisphenol A is concentrated. The thus-concentrated liquid residue is crystallized in the next step.

The condition for reduced-pressure distillation to concentrate bisphenol A is not specifically defined, for which, in general, the temperature may fall between 100 and 170° C. and the reduced pressure may fall between 40 and 500 Torr. If the temperature is lower than 100° C., the distillation step will require high vacuum; but if higher than 170° C., the next crystallization step will require superfluous heat removal.

Preferably, the concentration of bisphenol A in the concentrated liquid residue falls between 20 and 50% by weight, more preferably between 20 and 40% by weight. If its concentration is lower than 20% by weight, the recovery of bisphenol A will be low; but if higher than 50% by weight, the slurry after crystallization will be difficult to transfer to the next step.

The concentrated liquid residue obtained through the process as above is cooled to 40 to 70° C. Then, it is crystallized to be a slurry, giving a bisphenol A-phenol adduct (hereinafter referred to as "phenol adduct"). Cooling it may be attained, for example, by adding water to an external heat exchanger or to the crystallizer in which water evaporates while removing heat.

Next, the slurry of the concentrated liquid residue is filtered or centrifuged to separate the phenol adduct crystals from the mother liquid still containing by-products therein. The mother liquid may be directly or partly recycled in the reactor, or a part or all of it is decomposed with an alkali into phenol and isopropenylphenol and recovered. As the case may be, a part or all of the mother liquid could be isomerized and recycled for crystallization (see Japanese Patent Laid-Open No. 321834/1994).

The crystals of 1/1 adduct of bisphenol A/phenol thus obtained through the process as above are melted, when heated at 100 to 160° C., to be a liquid mixture.

From the liquid mixture, phenol is removed through distillation under reduced pressure, and a melt of bisphenol A is recovered. For the distillation, in general, the reduced pressure may fall between 10 and 100 Torr, and the temperature may fall between 150 and 190° C. If desired, phenol that may still in the product could be removed through steam stripping.

The melt of bisphenol A thus recovered is converted into liquid drops, then further cooled to be solid granules in a granulator such as a spray drier or the like. Its liquid drops are formed, for example, by spraying or spreading the melt, and then cooled and solidified with nitrogen, air or the like.

EXAMPLES

The invention is described more concretely with reference to the following Examples, which, however, are not intended to restrict the scope of the invention.

Example 1

Three packed columns each having an inner diameter of 20 mm and a height of 1,500 mm and filled with 90 cc of a sulfonic acid-type cation-exchange resin (Mitsubishi Chemical's Diaion-104H) were disposed in series (see FIG. 1). Each reactor was kept at 80° C. 250 cc/hr of phenol, 10 cc/hr of acetone, and ethylmercaptan in a molar ratio, acetone/ethylmercaptan of 6.7 were fed into the first reactor through its inlet; 7 cc/hr of acetone was into the second reactor through its inlet; and 7 cc/hr of acetone was into the third reactor through its inlet. The conversion of phenol at the outlet of each reactor was measured. It was 5.2% at the outlet of the first reactor, 8.3% at the outlet of the second reactor, and 15.5% at the outlet of the third reactor. The flow from the outlet of each reactor was sampled, and analyzed for its composition through liquid chromatography. From the data obtained, calculated was the phenol conversion.

COMPARATIVE EXAMPLE 1

Three packed tower columns each having an inner diameter of 20 mm and a height of 1,500 mm and filled with 90 cc of a sulfonic acid-type cation-exchange resin (Mitsubishi Chemical's Diaion-104H) were disposed in series (see FIG. 1) Each reactor was kept at 80° C. 250 cc/hr of phenol, 10 cc/hr of acetone, and ethylmercaptan in a molar ratio, acetone/ethylmercaptan of 20.0 were fed into the first reactor through its inlet; 7 cc/hr of acetone, and ethylmercaptan in a molar ratio, acetone/ethylmercaptan of 20.0 were into the second reactor through its inlet; and 7 cc/hr of acetone, and ethylmercaptan in a molar ratio, acetone/ethylmercaptan of 20.0 were into the third reactor through its inlet. The conversion of phenol at the outlet of each reactor was measured. It was 4.2% at the outlet of the first reactor, 7.2% at the outlet of the second reactor, and 14.7% at the outlet of the third reactor.

Comparing the data in Example 1 with those in Comparative Example 1, it is seen that the phenol conversion at the outlet of every reactor in Example 1 is all higher than in Comparative Example 1. From this, it is understood that, in the two where is used the same amount of the same catalyst, the phenol conversion is higher in Example 1 than in Comparative Example 1. This means that the catalyst can be used for a longer period of time in Example 1 than in Comparative Example 1.

As described in detail hereinabove with reference to its preferred embodiments, the present invention provides a method of producing bisphenol A in which the life of the acid-type ion-exchange resin used as a catalyst can be prolonged.

INDUSTRIAL APPLICABILITY

According to the invention, therefore, the reactor unit used can be continuously driven for a long period of time, and the production costs for bisphenol A can be reduced. In addition, the quality of the product, bisphenol A can be stabilized.

What is claimed is:

1. A method of producing bisphenol A by reacting phenol and acetone in the presence of an acid-type ion-exchange resin serving as a catalyst and an alkylmercaptan serving as a promoter, in which three or more reactors connected in series are used and all of phenol, all of an alkylmercaptan and a part of acetone are fed into the first reactor while the remaining acetone, divided into plural portions, is into all the second to the last reactors to produce bisphenol A.

2. The method of producing bisphenol A as claimed in claim 1, wherein the molar ratio of all acetone/alkylmercaptan falls between 10 and 25.

3. The method of producing bisphenol A as claimed in claim 1, wherein the molar ratio of phenol/all acetone falls between 6 and 13.

4. The method of producing bisphenol A as claimed in claim 1, wherein the acid-type ion-exchange resin is a sulfonic acid-type cation-exchange resin.

5. The method of producing bisphenol A as claimed in claim 1, wherein the alkylmercaptan is ethylmercaptan.

6. The method as claimed in claim 1, wherein said reactors are fixed-bed reactors.

7. The method as claimed in claim 1, wherein the temperature is from 65–95° C.

8. The method as claimed in claim 1, wherein a liquid hourly space velocity in each reactor falls between 0.5 and 6 hr.$^{-1}$.

9. The method as claimed in claim 1, further comprising distilling a reaction product in a distillation column.

10. A method of producing bisphenol A comprising
reacting phenol and acetone in the presence of an acid-type ion-exchange resin serving as a catalyst and an alkylmercaptan serving as a promoter, wherein three or more reactors connected in series are used,
feeding all of said phenol, all of an alkylmercaptan and a part of said acetone into a first reactor, while
feeding the remaining acetone, divided into plural portions, into all of a second reactor to a last reactor to produce bisphenol A,
wherein a molar ratio of all of said acetone to said alkylmercaptan falls between 10 and 25, and
wherein a molar ratio of said phenol to all of said acetone falls between 6 and 13.

11. The method of producing bisphenol A as claimed in claim 10, wherein the acid-type ion exchange resin is a sulfonic acid cation-exchange resin.

12. The method of producing bisphenol A as claimed in claim 10, wherein the alkyl mercaptan is ethyl mercaptan.

13. The method as claimed in claim 10, wherein said reactors are fixed-bed reactors.

14. The method as claimed in claim 10, wherein the temperature is from 65–95° C.

15. The method as claimed in claim 10, wherein a liquid hourly space velocity in each reactor falls between 0.5 and 6 hr.$^{-1}$.

16. The method as claimed in claim 10, further comprising distilling a reaction product in a distillation column.

* * * * *